United States Patent [19]

Bercik et al.

[11] Patent Number: 4,741,815

[45] Date of Patent: May 3, 1988

[54] APPARATUS FOR INDICATION OF THE FINAL STAGE OF A TITRATION ANALYSIS

[75] Inventors: Juraj Bercik; Jan Dzurov; Leos Vyskocil, all of Bratislava, Czechoslovakia

[73] Assignee: Slovenska vysoka skola technicka, Bratislava, Czechoslovakia

[21] Appl. No.: 37,316

[22] Filed: Apr. 13, 1987

Related U.S. Application Data

[63] Continuation-in-part of Ser. No. 870,139, Jun. 2, 1986, abandoned.

[30] Foreign Application Priority Data

May 31, 1985 [CS] Czechoslovakia ............... 3907-85
May 31, 1985 [CS] Czechoslovakia ............... 3908-85

[51] Int. Cl.$^4$ ............................................. G01N 31/16
[52] U.S. Cl. .................................... 204/405; 422/75; 436/51
[58] Field of Search ............... 204/1 M, 405, 406, 412; 436/51; 422/75

[56] References Cited

U.S. PATENT DOCUMENTS

| | | | |
|---|---|---|---|
| 3,248,309 | 4/1966 | Robinson | 204/405 X |
| 3,950,237 | 4/1976 | Arakawa et al. | 204/405 |
| 4,018,565 | 4/1977 | Fletcher et al. | 204/405 X |
| 4,059,406 | 11/1977 | Fleet | 204/412 X |
| 4,203,156 | 5/1980 | Ishikawa | 204/405 X |
| 4,426,621 | 1/1984 | Galwey et al. | 324/439 |
| 4,498,039 | 2/1985 | Galwey et al. | 324/234 |

OTHER PUBLICATIONS

Donald T. Sawyer et al., "Experimental Electro-Chemistry for Chemists", pp. 395–428, (1974).
C. E. Champion et al., Anal. Chem., vol. 42, No. 11, pp. 1210–1213, (1970).
W. Donald Cooke et al., Anal. Chem., vol. 23, No. 11, pp. 1662–1667, (1951).
David J. Myers et al., Anal. Chem., vol. 46, No. 3, pp. 356–359, (1974).

Primary Examiner—G. L. Kaplan
Attorney, Agent, or Firm—Klein & Vibber

[57] ABSTRACT

An apparatus for electrochemical indication of the final stage of a titration analysis has a first indication electrode located in an electrochemical titration container connected by a switch to a sampling current amplifier feeding a recorder. Both the amplifier and the switch are controlled by a timing circuit which causes the switch to connect and disconnect the electrode to the amplifier. By only connecting the electrode to the amplifier for a brief time and activating the amplifier for a brief time thereafter, the instantaneous value of indication current is obtained. During the remaining time period, the indication electrode is galvanically disconnected from the amplifier and consequently, no reduction of concentration of electroactive substance in the proximity of the electrode occurs and an extremely high current response is attained. In operation of the apparatus, there is also effectively suppressed the undesirable charging current since the indication electrode, once disconnected, does not lose but a neligible portion of electric charge. The high sensitivity of the apparatus is achieved, according to the invention, in connection with both the single and two indication electrodes.

6 Claims, 3 Drawing Sheets

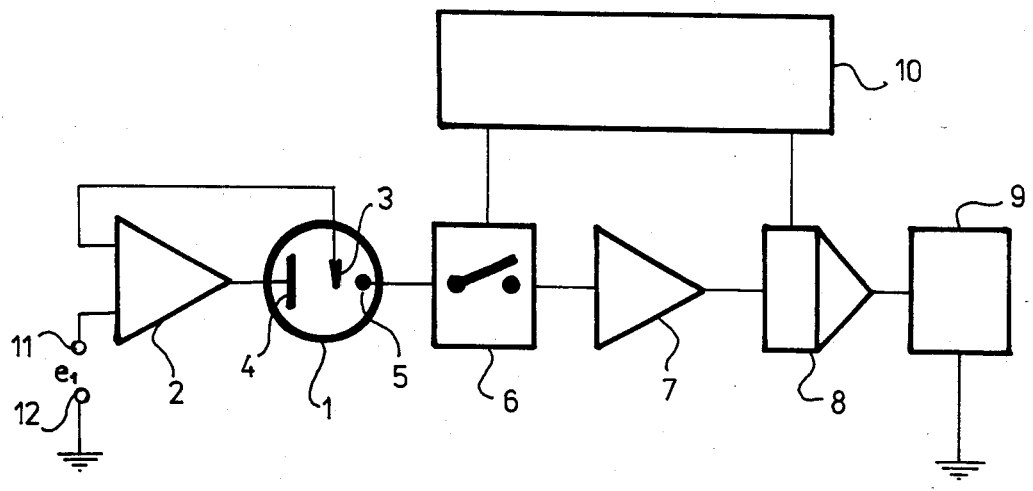
FIG.1
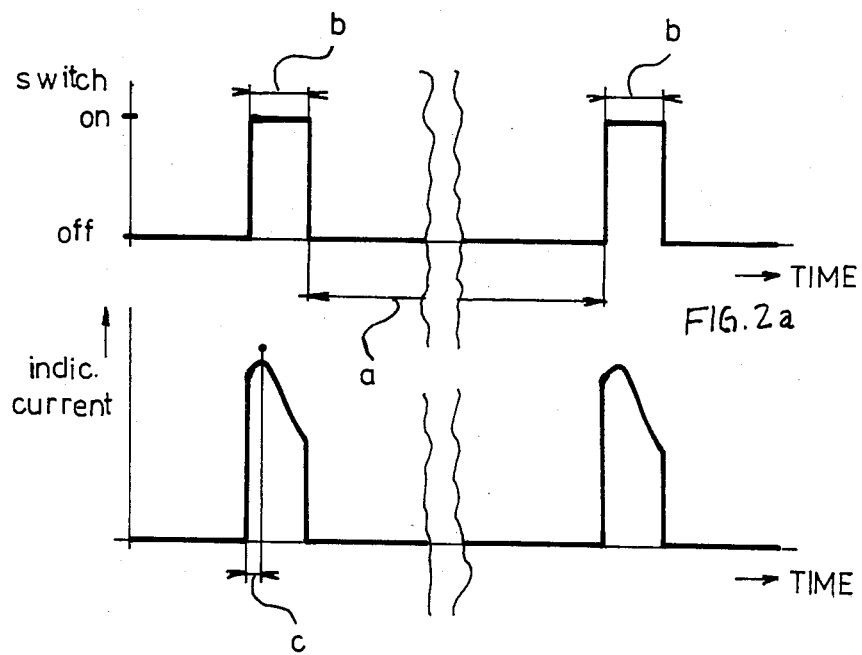
FIG.2a
FIG.2b

APPARATUS FOR INDICATION OF THE FINAL STAGE OF A TITRATION ANALYSIS

This application is a continuation-in-part of Ser. No. 870,139, filed June 2, 1986 and now abandoned.

FIELD OF THE INVENTION

This invention relates to the indicator of the final stage or end-point of a titration analysis by an electrochemical impulse method.

BACKGROUND OF THE INVENTION

The most important step of a titration analysis is the determination of the final stage or end-point of the titration. It is the state in which the amounts of the substance to be analyzed and of the titrating agent are balanced. Among various known methods of indication of the titration end-point, there are visual, photometric, electrochemical and others. The accuracy, correctness and the available concentration limits depend on the sensitivity of such methods. One of the most sensitive electrochemical methods is the amperometric indication based on one or two indication electrodes. These methods permit titrations up to concentrations of $10^{-5}$ to $10^{-6}$ mol/l and in certain very specific cases up to $10^{-7}$ mol/l. See e.g. Cooke, Reilley, Furman, "Sensitive End-Point Procedure for Coulometric Titrations," 23 Anal. Chem. 1662 (November 1951), and, Myers, Osteryoung, "Amperometric Titrations Employing Differential Pulse Polarography," 46 Anal. Chem. 356, (March 1974). Concentrations of up to $5 \times 10^{-8}$ mol/l are also known in connection with coulometric titrimetry. See: Champion, Marinenko, Taylor, "Determination of Submicrogram Amounts of Chromium by Coulometric Titrimetry," 42 Anal. Chem. 1210, (September 1970).

The limiting factors in known apparatuses for amperometric indication of the end-point of titration are the low current signals produced at low-level concentrations of the substances to be analyzed, the unfavorable signal to noise ratio and some disturbing background currents from which particularly the capacitive charging current limits the concentration limit and the sensitivity of the titration.

PRIOR ART PATENTS

U.S. Pat. Nos. 4,426,621 and 4,498,039, (Galwey et al) disclose a Detection Circuitry for Electrochemical Analysis and an Instrument for Use with An Electrochemical Cell, respectively. The high sensitivity of the present invention, however, is achieved in that the indication electrode is disconnected and that it is connected to the measuring circuit for a very short time period, and particularly by a switch connected within the indication electrode circuit. As clearly results from the two references, the indication electrode is permanently connected to the measuring circuit. In this point but also by their wiring mode and the effect attained, the two references distinguish from the present invention.

U.S. Pat. No. 4,059,406 (Fleet) relates to the structure and operation of an electrochemical detector. Similarly, as in the previous case, the electrodes are permanently connected to the measuring circuit whereby the reference distinguishes from the claimed subject matter. Since the indication current is not interrupted by disconnecting the electrode from the measuring circuit, the apparatus cannot reach such effects as the claimed one.

SUMMARY OF THE INVENTION

It is an object of the invention to provide an apparatus for indication of the final stage of a titration analysis having increased sensitivity when compared to known amperometric indication methods. The high sensitivity of this apparatus is achieved, according to the invention, in that a polarization voltage is applied to an indication electrode only for a short time necessary for measuring the insantaneous value of indication current. During the remaining time period, the indication electrode is galvanically disconnected by means of a switch. Consequently, no reduction of concentration of electroactive substance in the proximity of working electrode occurs and an extremely high current response is attained. In operation of the apparatus, there is also effectively suppressed the undesirable charging current since the indication electrode, once disconnected, does not lose but a neligible portion of electric charge. The high sensitivity of the apparatus is achieved, according to the invention, in connection with both the single and two indication electrodes.

BRIEF DESCRIPTION OF THE DRAWING

FIG. 1 is a block diagram of the apparatus circuitry based on a three-electrode system;

FIG. 2a is a time-sequence chart showing the operation of a switch and a sampling amplifier;

FIG. 2b is a time-sequence chart showing the behavior of indication current;

DESCRIPTION OF THE PREFERRED EMBODIMENTS

Figure 3:
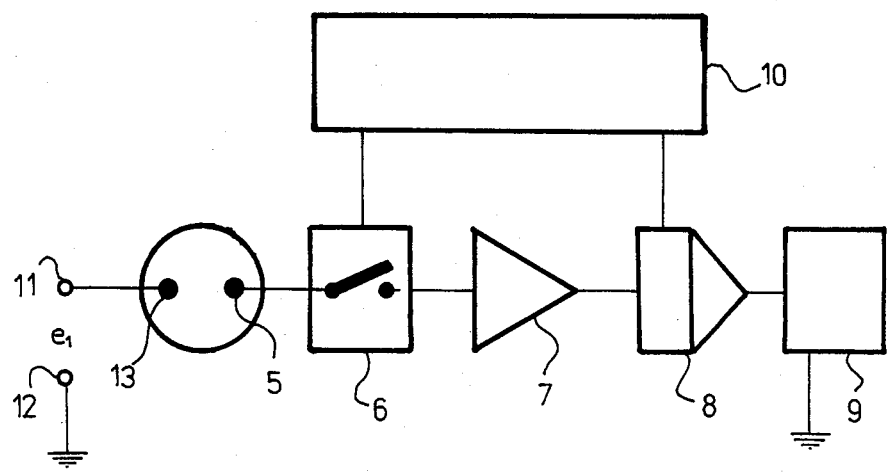
FIG. 3 is a block diagram of the apparatus circuitry based on a pair of indication electrodes.

Referring to FIG. 1, a three-electrode indication system is shown in an electrochemical titration container 1, said system comprising an auxiliary electrode 4, a reference electrode 3 and an indication electrode 5. The indication electrode 5 is connected in series with a switch 6. When the switch 6 is in the on position, a voltage $e_1$ applied between the input 11 of a potentiostat 2 and an earth terminal 12, is maintained between the indication electrode 5 and the reference electrode 3 by means of the potentiostat 2. The operation of switch 6 is controlled by a timing device 10 in accordance with the time-sequence chart shown in FIG. 2a. During the time period a, the switch is in off-position while, during a short period b, it is in on-position. The current flowing through the indication electrode 5 is shown in FIG. 2b. This current is measured by a current to voltage converter 7 (FIG. 1), and its instantaneous value, within a time period c from the on-switching of the switch 6 is taken by a sampling amplifer 8 which is also controlled by the timing device 10. The indication signal is registered by a recorder 9.

As to the voltage converter 7 and sampling amplifier 8, their structure is not involved in the claimed subject matter, and any suitable, commercially available types such as the National Semiconductor integrated circuit LF 198 may be used.

According to known amperometric indication methods, the indication electrode is permanently connected to the polarization voltage. In the apparatus shown in FIG. 1, this is the state wherein the switch 6 is always in on-position. Due to the permanent current flow, a markedly reduced concentration of electroactive substance in the proximity of the indication electrode occurs. Since the indication signal directly depends on the concentration of electroactive substance in the proximity of the indication electrode, it is substantially lower than in the case of the present invention.

As can be seen in FIG. 2, the current flows through the indication electrode 5 for the short time period b only. During the time period a, which is substantially longer than the period b, the indication electrode 5 is galvanically disconnected by the switch 6. Therefore, no reduction of electroactive substance concentration occurs in the proximity of indication electrode 5, due to the indication current. Thus, the indication signal is substantially increased as compared to the prior art.

Since the indication electrode 5 is, in off-position of switch 6, disconnected from the input of the current to voltage converter 7, it keeps its electric charge during the time period a. Consequently, the current flowing through the indication electrode 5, after switching on the switch 6, contains only a minimum portion of charging or capacitive component. This means that the apparatus of the invention, apart from the above mentioned increase of indication current, effectively suppresses the disturbing charging component of this current. Owing to the two effects, the indication signal registered by the recorder 9 is substantially higher than that attained by the known methods whereby the sensitivity of detection of electroactive substances and of the titration end-point are substantially increased.

In the apparatus shown in FIG. 3, a pair of indication electrodes 5 and 13 are used. When the switch 6 is permanently in on-position, an orthodox bi-amperometric indication is obtained. According to the present invention, however, the switch 6 and the sampling amplifier 8 are controlled in accordance with the time-sequence chart in FIG. 2. In spite of the fact that the mechanism of current response production is somewhat different, the resulting effect is analogous to that attained in the apparatus shown in FIG. 1, which means a marked increase of the indication signal. An advantage of the apparatus shown in FIG. 3 is that the reference electrode is omitted.

EXAMPLE 1

Figure 4:
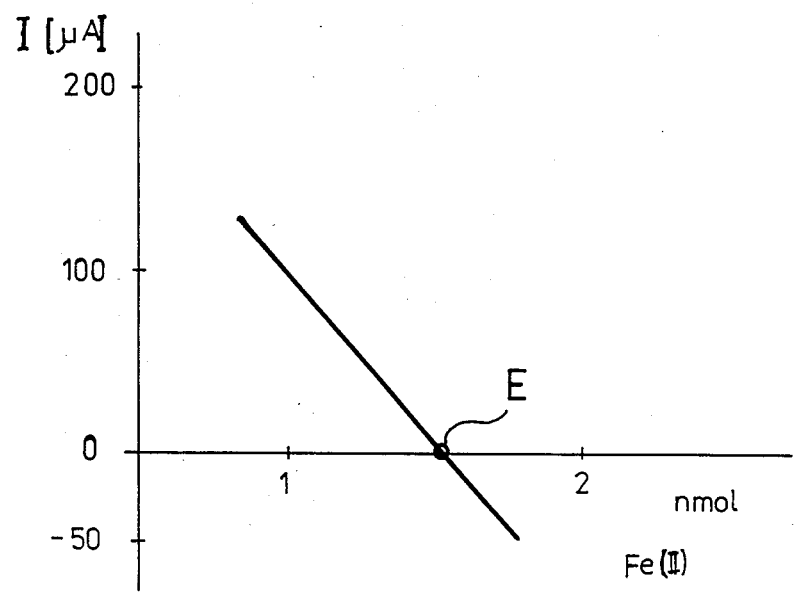
FIG. 4 is a diagram of the determination of titration end-point in the apparatus with three electrodes.

A tetravalent cerium content in a solution was to be determined. The titration was carried out with bivalent iron ions which were coulometrically generated. As indication electrode, a platinum electrode was used. A potential of 0.82 V was excited against 1 M argentochloride electrode. For the indication there was used the apparatus shown in FIG. 1 and having the following parameters: time period a=100 ms, time period b=0.1 ms, time period c=0.02 ms. The titration end-point E was indicated on the current passage through zero (FIG. 4). There was achieved a concentration limit determination of to $4 \times 10^{-9}$ mol/l, the determination error not having exceeded 9 percent.

EXAMPLE 2

Figure 5:
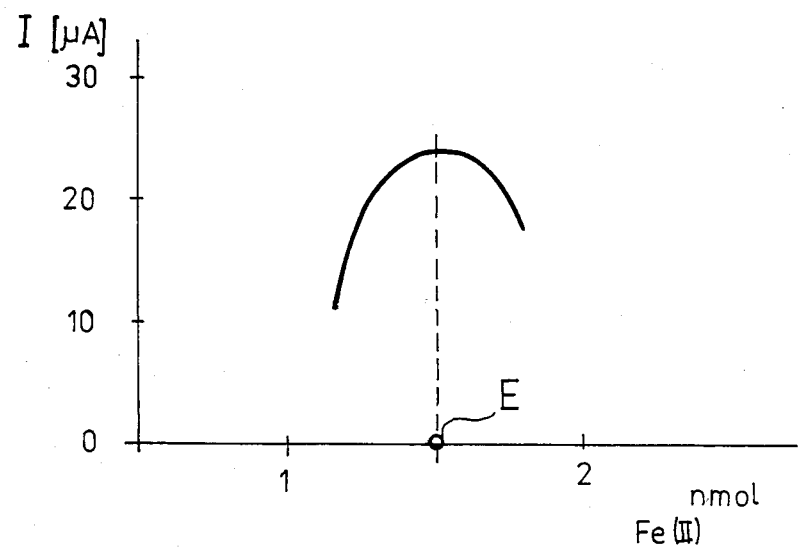
FIG. 5 is a similar diagram in connection with the apparatus having two indication electrodes.

The same system as in Example 1 was analyzed while using the apparatus shown in FIG. 3. To a pair of platinum indication electrodes there was applied a potential $e_1 = 0.085$ V. The time periods a, b, and c, respectively, were the same as in Example 1. The titration end-point was determined on the basis of top of the curve in FIG. 5. There was attained the determination of concentration limit of $9 \times 10^{-9}$ mol/l, the determination error not having exceeded 10 percent.

INDUSTRIAL APPLICABILITY

The present invention can be preferably availed of in all types of titration analyses, especially in cases of low and very low concentrations, i.e. in the field of trace element analysis, in laboratories of quality inspection, in food, chemical, and pharmaceutic industries, in health service, in analysis of special materials and in environmental inspection. Moreover, the invention is applicable in high-sensitive electrochemical detectors used for analytical separation processes such as HPLC, LC, or the like.

We claim:

1. An apparatus for electrochemical indication of the final stage of a titration analysis, comprising
   a first indication electrode located in an electrochemical titation container;
   a timing circuit;
   a sampling current amplifier having an input and an output and being activated by said timing circuit;
   a switch activated by said timing circuit, said switch connecting and disconnecting said indication electrode to the input of said amplifier;
   a recorder, connected to the output of said amplifier whereby the output of said amplifier is recorded;
   whereby the indication electrode is periodically connected by the switch to the sampling current amplifier, and a current sample is measured just after connecting the indication electrode.

2. An apparatus as claimed in claim 1, further comprising an auxiliary electrode and a reference electrode located in said container; and
   a potentiostat connected to a source of polarization voltage;
   said auxiliary electrode and reference electrode both being connected to said potentiostat, whereby both said auxiliary electrode and reference electrode are provided with a polarization voltage.

3. An apparatus as claimed in claim 2, wherein said timing circuit controls said switch and said amplifier so that every 100 ms, said switch is activated to connect said first indication electrode to said amplifier for 0.1 ms and immediately following the activation of said switch, said amplifier is activated for 0.02 ms.

4. An apparatus as claimed in claim 1, further comprising a second indication electrode located in said container, a source of polarization voltage being connected to said second indication electrode.

5. An apparatus as claimed in claim 4, wherein said timing circuit controls said switch and said amplifier so that every 100 ms, said switch is activated to connect said first indication electrode to said amplifier for 0.1 ms and immediately following the activation of said switch, said amplifier is activated for 0.02 ms.

6. An apparatus as claimed in claim 1, wherein said timing circuit controls said switch and said amplifier so that every 100 ms, said switch is activated to connect said first indication electrode to said amplifier for 0.1 ms and immediately following the activation of said switch, said amplifier is activated for 0.02 ms.

* * * * *